(12) United States Patent
Bono et al.

(10) Patent No.: US 11,166,783 B2
(45) Date of Patent: Nov. 9, 2021

(54) ROBOTIC BASE WITH CONTROLLED MOVEMENT FOR SURGICAL PROCEDURES

(71) Applicant: Peter L. Bono, Bingham Farms, MI (US)

(72) Inventors: Peter L. Bono, Bingham Farms, MI (US); James D. Lark, West Bloomfield, MI (US); John S. Scales, Ann Arbor, MI (US)

(73) Assignee: Peter L. Bono, Bingham Farms, MI (US)

( * ) Notice: Subject to any disclaimer, the term of this patent is extended or adjusted under 35 U.S.C. 154(b) by 184 days.

(21) Appl. No.: 16/676,203

(22) Filed: Nov. 6, 2019

(65) Prior Publication Data

US 2020/0138544 A1 May 7, 2020

Related U.S. Application Data

(60) Provisional application No. 62/757,139, filed on Nov. 7, 2018.

(51) Int. Cl.
| | |
|---|---|
| *B62D 63/04* | (2006.01) |
| *A61B 90/50* | (2016.01) |
| *A61B 34/30* | (2016.01) |
| *B25J 5/00* | (2006.01) |
| *B60B 19/00* | (2006.01) |
| *B60B 19/12* | (2006.01) |
| *B60G 17/08* | (2006.01) |
| *B60K 7/00* | (2006.01) |

(52) U.S. Cl.
CPC .............. *A61B 90/50* (2016.02); *A61B 34/30* (2016.02); *B25J 5/007* (2013.01); *B60B 19/003* (2013.01); *B60B 19/12* (2013.01); *B60G 17/08* (2013.01); *B60K 7/0007* (2013.01); *B62D 63/04* (2013.01); *B60K 2007/0084* (2013.01)

(58) Field of Classification Search
CPC .......... A61B 90/50; A61B 34/30; B25J 5/007; B60B 19/003; B60B 19/12; B60K 7/007
See application file for complete search history.

(56) References Cited

U.S. PATENT DOCUMENTS

| | | | |
|---|---|---|---|
| 3,876,255 A | 4/1975 | Ilon | |
| 6,547,340 B2 | 4/2003 | Harris | |
| 7,980,335 B2 * | 7/2011 | Potter | ................. B66F 9/07577 180/7.1 |
| 9,248,876 B2 * | 2/2016 | Nuchter | ................... B25J 5/007 |
| 2010/0187779 A1 * | 7/2010 | Potter | ................. B66F 9/07577 280/5.514 |

(Continued)

FOREIGN PATENT DOCUMENTS

| | | |
|---|---|---|
| EP | 3257463 | 12/2017 |
| KR | 101740921 | 5/2017 |

*Primary Examiner* — John D Walters
*Assistant Examiner* — James J Triggs
(74) *Attorney, Agent, or Firm* — McHale & Slavin, P.A.

(57) ABSTRACT

The invention involves a system and method for controlling the movements of a multi-axis robot to perform a surgery at least on the spinal area of a human in vivo. The system includes controls and software coding to cause the robot to move in desired patterns to complete the surgery, which may include bone, disc and tissue removal, and may also include insertion of hardware for fusing adjacent bony structures.

14 Claims, 5 Drawing Sheets

(56) References Cited

U.S. PATENT DOCUMENTS

2011/0070998 A1\* 3/2011 Takenaka .............. B60B 19/125
 476/68
2012/0101508 A1\* 4/2012 Wook Choi ........... A61B 34/30
 606/130

\* cited by examiner

ROBOTIC BASE WITH CONTROLLED MOVEMENT FOR SURGICAL PROCEDURES

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/757,139 entitled "ROBOTIC BASE WITH CONTROLLED MOVEMENT FOR SURGICAL PROCEDURES", filed Nov. 7, 2018. The contents of the above referenced application is incorporated herein by reference in its entirety.

FIELD OF THE INVENTION

The invention relates to robotic surgical procedures and, more specifically, to a robotic base that, in addition to traversal of a surgical robot, provides a suspension and elevation control movements to complete a surgical procedure.

BACKGROUND INFORMATION

The performance of a surgical procedure on the spine with the assistance of a robot is known in the art. However, the surgeries that have been previously performed are generally small portions of the surgery, or have been small steps in the overall completion of the surgery. These robots are only manually positionable, and the reach of the robot is limited. Thus, the known robotic surgical systems are deficient for complex and delicate procedures such as bone removal, disc removal and the like.

Therefore, the present invention provides a robotic truck base which overcomes the disadvantages of prior art robotic surgical systems. The robotic truck base of the present invention not only provides for relative ease in the setup of the surgical procedure and control over the robot during the actual operation, it also provides movement, a suspension and controlled movement of the robot during the surgery. One embodiment provides tilting or raising of the robotic truck base during the surgery to aid the robot in reaching desired portions of the anatomy at a desired trajectory. The moveable base also provides a suspension to the truck base to smooth the movements of the truck base as it rolls over uneven surfaces.

SUMMARY OF THE INVENTION

Briefly, the invention involves a robotic truck base and method for controlling the movements of the robotic truck base to move a multi-axis robot to perform a surgery at least on the spinal area of a human in vivo. The robotic truck base is constructed so that the robot can be repositioned under power during a surgery to provide better reach and access to the robotic arm. A suspension is provided so that the movements are smooth, even on uneven surfaces. Lifters are provided which allow the robot to raise or tilt the base for better access to the surgical site. The system includes controls and software coding to cause the robotic truck base to move in desired patterns to complete a surgery, which may include bone, disc and tissue removal, and may also include insertion of hardware for fusing adjacent bony structures.

Accordingly, it is an objective of the present invention to provide a robotic truck base for a multi-axis surgical robot for performance of a surgical procedure.

It is a further objective of the present invention to provide a software controlled robotic truck base for a multi-axis robot for performance of a surgical procedure.

It is yet a further objective of the present invention to provide a method for controlling the movement of a robotic truck base of a multi-axis robot for the purpose of performing a surgical procedure.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENTS

Figure 1:
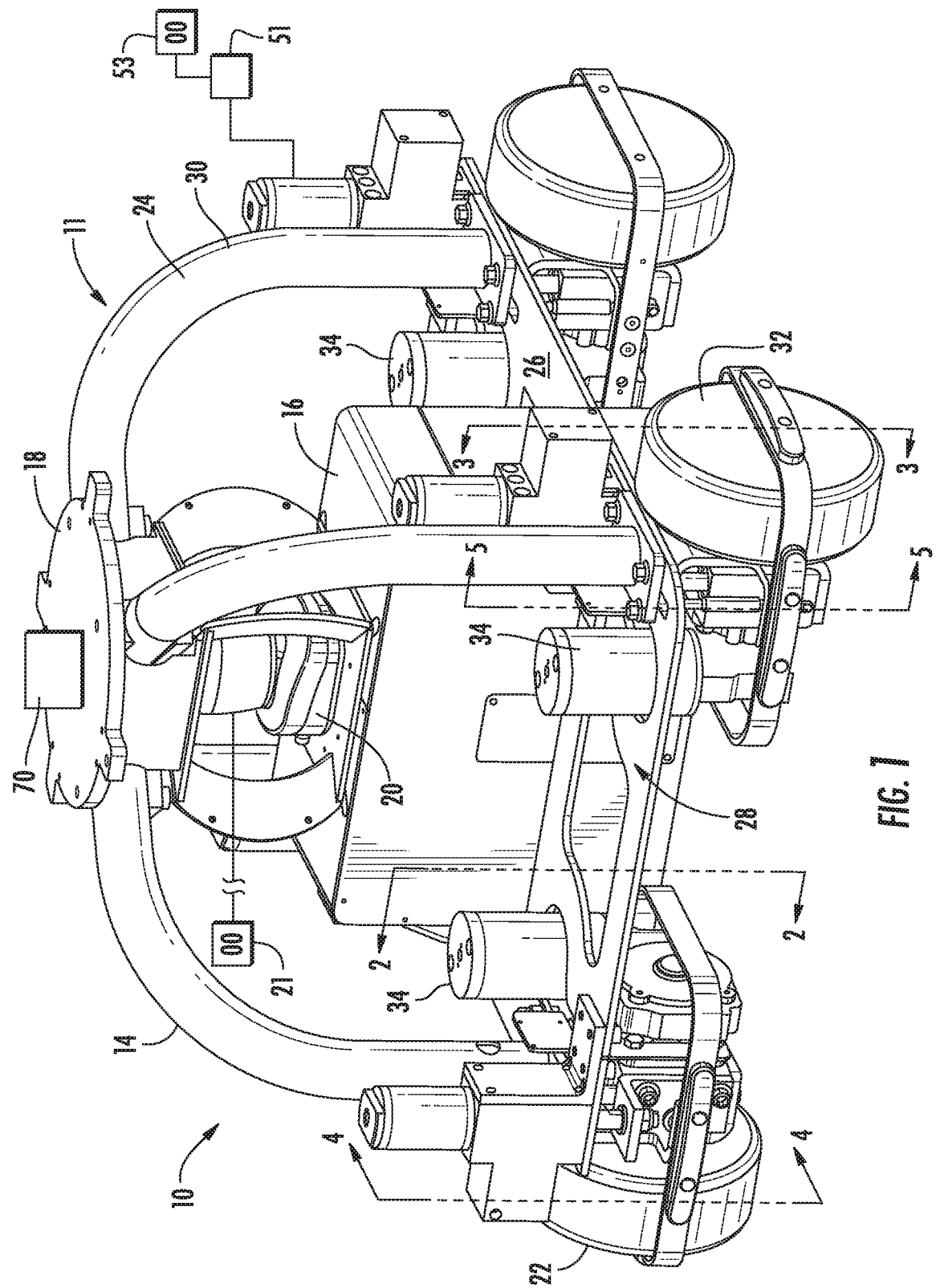
FIG. 1 is a front right perspective view, illustrating the robotic truck base of the present system.
Figure 2:
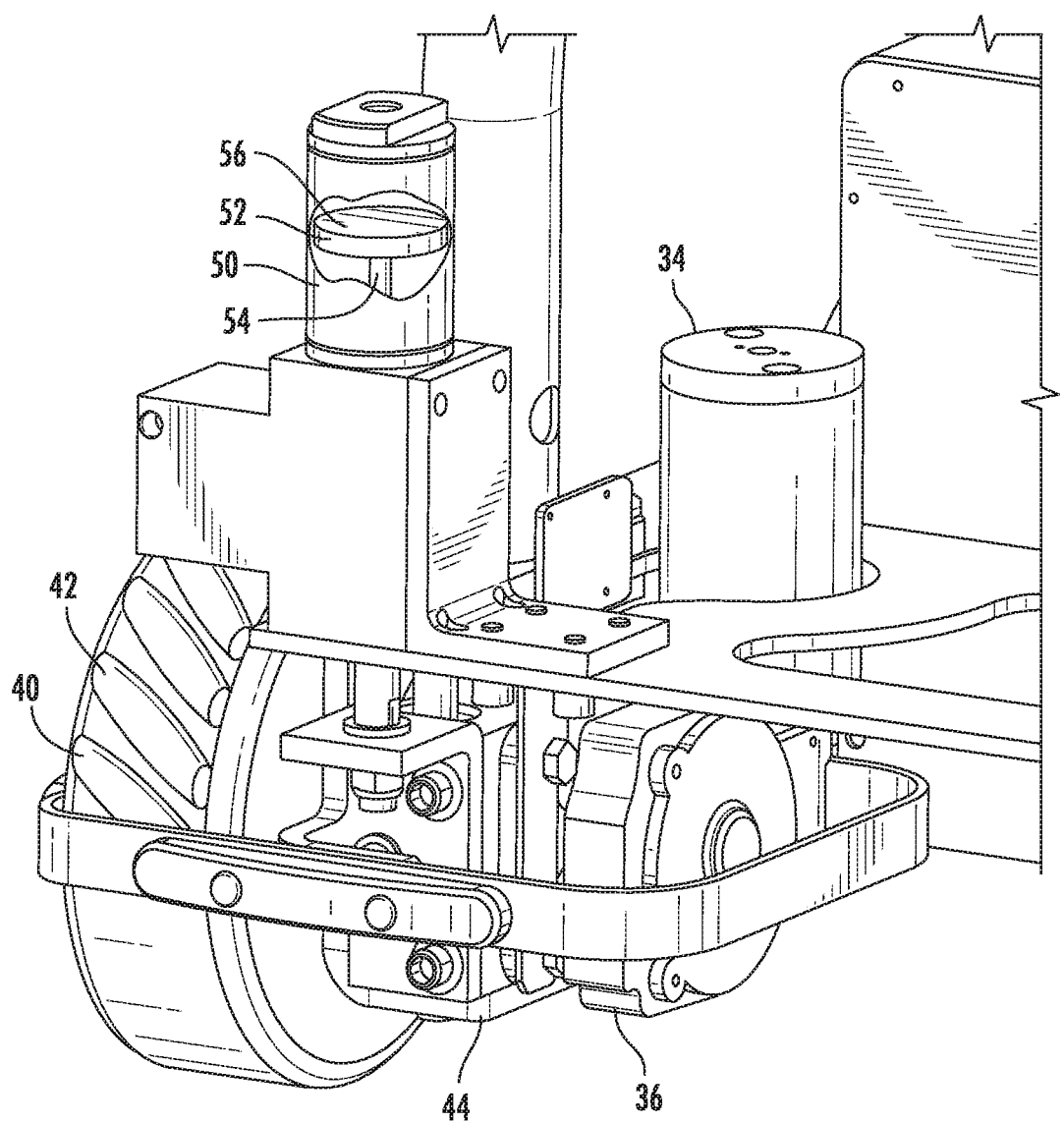
FIG. 2 is a partial view taken along lines 2-2 of FIG. 1, illustrating a wheel assembly of the robotic truck base.
Figure 3:
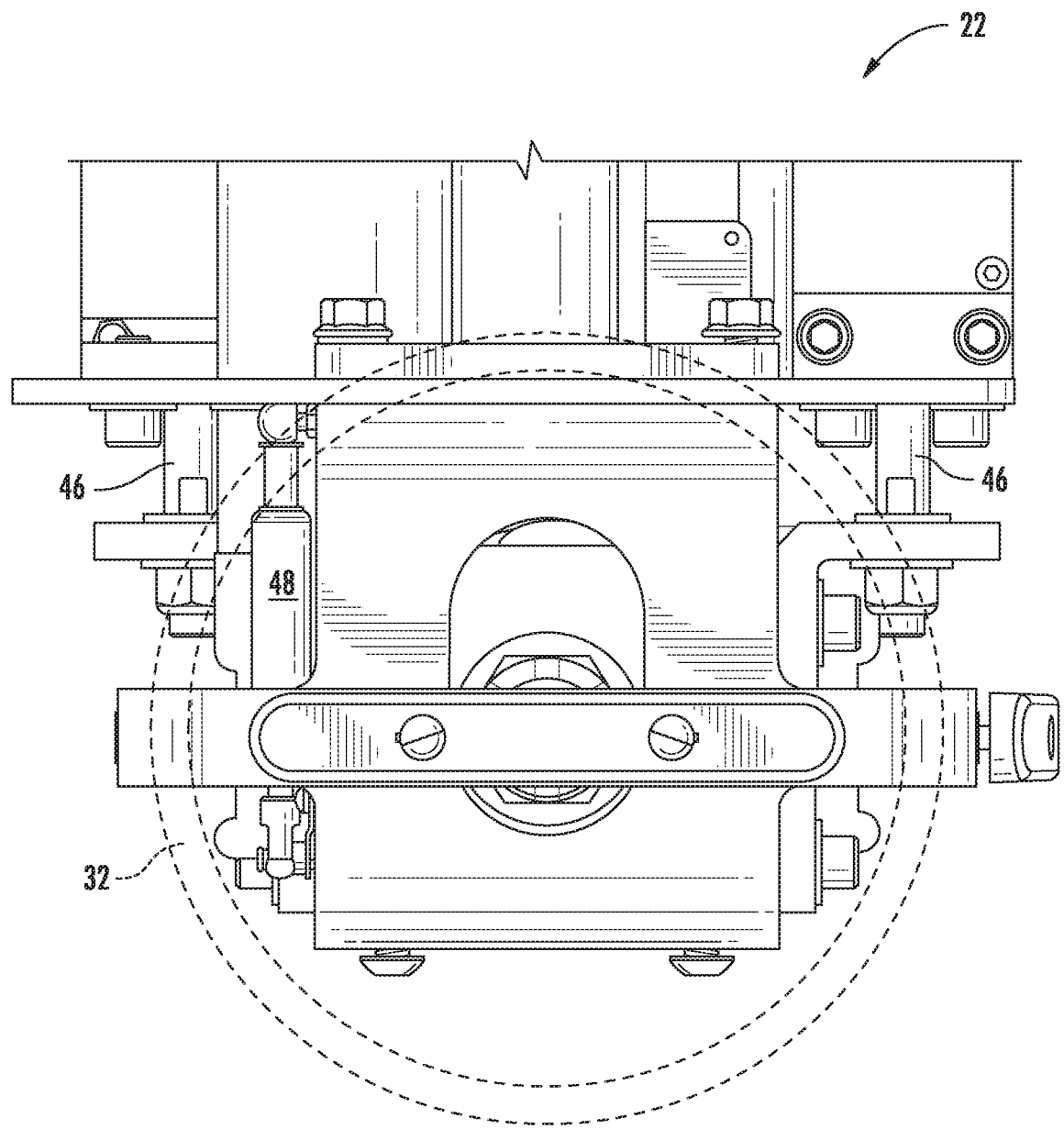
FIG. 3 is a partial view taken along lines 3-3 of FIG. 1, illustrating portions of the suspension for the wheel assemblies of the robotic truck base.
Figure 4:
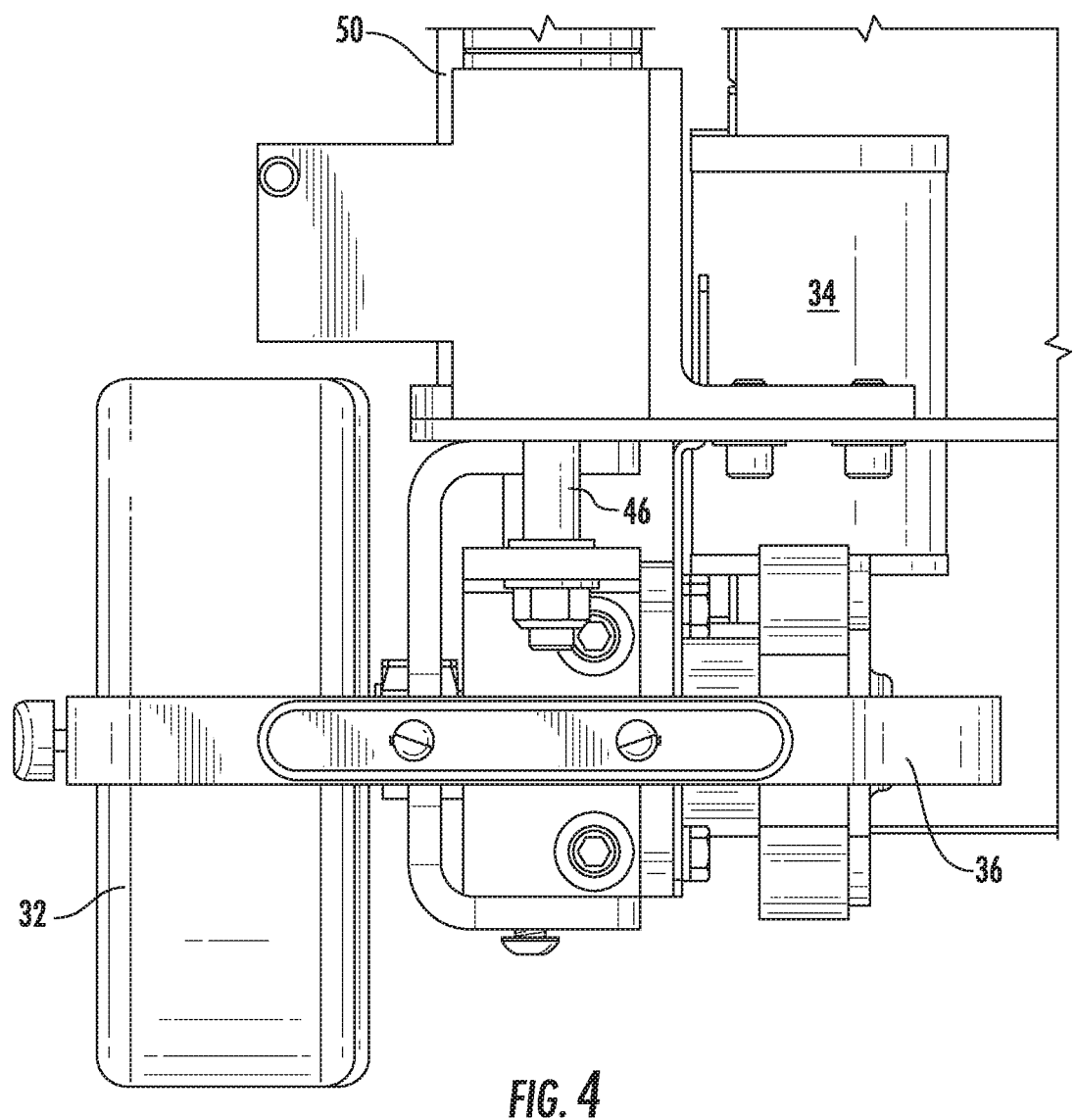
FIG. 4 is a partial view taken along lines 4-4 of FIG. 1, illustrating a front view of one wheel assembly of the robotic truck base.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 5:
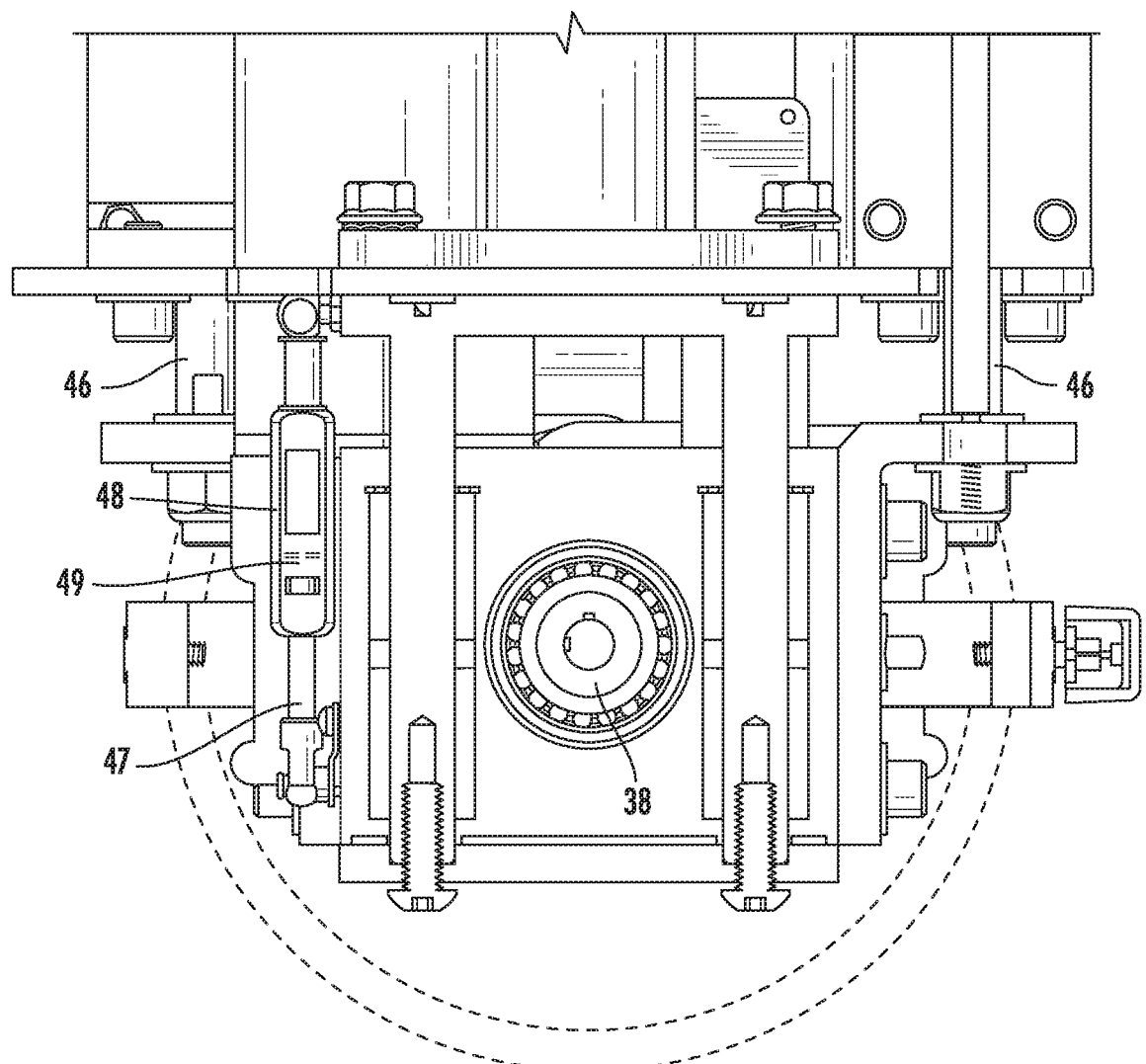
FIG. 5 is a partial view taken along lines 5-5 of FIG. 1, illustrating a rear view of one wheel assembly of the robotic truck base.

Referring generally to FIGS. 1-5, a robotic surgical base 10 for providing movement to a multi-axis automotive style robot 12 to perform a surgical procedure on a human patient in vivo is illustrated. One such suitable robot is made by KUKA Robotics Corporation of Augsburg Germany. The robotic base 10 includes a truck 11 including a frame 14 having a power supply 16, which may be a battery or other storage device, a support platform 18, an electronic controller 20 and a plurality of wheel assemblies 22. The controller 20 can be connected to a manually operated control element 21, allowing surgical personnel to manually effect movement of the truck 11 and associated robot 12. The power supply 16 may be mounted to the truck 11 or may be remote from the truck 11, using, for example, an attached cord. The frame 14 is generally a space-frame constructed from a combination of tubular 24 and sheet 26 materials to form a substantially rigid structure suitable to support a multi-axis robot 12. The frame 14 may be constructed from any suitable metal, such as steel or aluminum or a combination thereof. Alternatively, the frame 14 may be constructed from polymer based materials, such as fiberglass or carbon fiber, without departing from the scope of the art. In the preferred embodiment, the truck 11 also includes a base plate 28 formed from sheet 26 material connecting to a plurality of arms 30 at a lower portion of the arms. A plurality of wheel assemblies 22 are mounted to the truck 11, as by being secured to the base plate 28. The wheel assemblies 22 are preferably Mecanum wheels 32 which allow movement of the robot in any direction without rotation of the wheel about a vertical axis. Mecanum wheels 32 and their operation are disclosed in U.S. Pat. Nos. 3,876,255, 6,547,340 and 7,980,335, the disclosures of which are incorporated herein by reference regarding the general concept of such wheels. While the preferred wheel embodiment is described as using Macanum wheels, other wheels known to one of skill in the art may be used. The wheels 32 are driven by a drive motor 34 connected to a gear box 36 having a pair of output shafts 38 (FIG. 5). The output shafts 38 are preferably arranged one around the other so that the shafts have the same longitudinal axis. In this manner, one shaft can independently drive the wheel hub 40, while the other shaft can independently drive the rollers 42. The wheel hubs 40 preferably provide forward and backwards movement to the robotic base 10, while the rollers 42 provide left and right directional movements. It should also be noted that both the wheel hub 40 and the rollers 42 can be operated simultaneously to provide angular or rotational movement as desired. It is to be understood that the wheels 32 can be alternatively driven by a single shaft as disclosed in the herein referenced patents. In the preferred embodiment, the wheels 32 should be provided with drive motors 34 and sensors that provide feedback to the controller 20, which has the capability to monitor the movement, and alter the movement, in real time based upon discrepancies such as wheel slippage and the like.

Still referring to FIGS. 1-5, the wheel assemblies 22 are constructed and arranged to move on a suspension as a complete assembly. In this manner, the wheel assemblies are suitable to smooth, rough or uneven floors and terrain to reduce movement and vibration being transferred to the robot 12. In one embodiment, the wheel assembly 22 moves up and down on guide pins 46 (FIGS. 3 and 5) having a fluid charged device, such as a gas charged cylinder 48, supporting the weight of the robotic base 10 and robot 12. The gas charged cylinder 48 may also be constructed and arranged to provide damping to the movements of the wheel assembly 22. The gas charged cylinder 48 includes a gas cylinder piston 49 connected to a gas cylinder rod 47 which moves the piston to compress the gas contained in the gas charged cylinder 48. A pressure fluid system, designated generally 51, can be operably connected to the cylinders 48 to effect their operation. Such a system 51 can include a pump with motor, or simply be a pressurized tank. Such a system can pressurize a gas or liquid. Suitable piping and valving can connect the system 51 to the cylinders 48. The system 51 can be controlled by the controller 20, the below described controller and/or a manual controller 53. In another embodiment, hydraulic cylinder(s) 50 may be constructed to allow the wheel assembly 22 to "float", e.g. be weight supported and move up and down, whereby the hydraulic piston 52 in the hydraulic cylinder 50 is allowed to move up and down with the wheel assembly 22. A hydraulic rod 54 is connected to the piston 52 to move simultaneously therewith. This construction allows the hydraulic cylinder 50 to be locked by preventing movement of hydraulic fluid 56 within the hydraulic cylinder 50. This construction provides rigidity to the robot by removing the movement of the suspension. This construction also allows the hydraulic cylinders 50 to be selectively extended and retracted to raise, lower or angle the truck 11 and mounted robot 12 as desired to provide advantageous positioning to the robotic arm for surgical procedures. Movement of the hydraulic cylinders 50 may be provided by an electric over hydraulic pump operated by the controller 20 to switch modes of operation or provide the lifting, lowering or angle operations. Alternatively, a device such as a gas over hydraulic intensifier may be utilized to allow the hydraulic cylinders 50 to float, as well as lift or lower, by application of pressurized gas to the intensifier as is known in the hydraulic arts. In at least one embodiment, the hydraulic cylinders 50 are provided with feedback to the controller 20 so that the controller can monitor the relative vertical positioning of the hydraulic cylinder 50. It should be noted that, while guide pins 46 are illustrated as guiding the wheel assemblies 22 for movement, guide plates, pivots, dove tails, guide ways and the like may be utilized to guide wheel assemblies 22 throughout their movement in providing a suspension to the robotic base 10.

Still referring to FIGS. 1-5, in at least one embodiment, the robotic base is constructed and arranged to move out of the way of a surgeon upon receiving a verbal or hard command (microphone, button, touch screen or the like) to allow the surgeon to access the patient to complete a portion of the procedure or any other task for which the surgeon needs access to the patient anatomy. Because the wheel assemblies include feedback to the controller 20, the robotic base can easily return to the position it was in before being moved.

The surgical robot 12 can also include an electronic programmable controller 70 interfaced with the controller 20 to instruct the truck 11 how to move during or before a surgery to better position the robot for surgery. The instruction for movement of the truck 11 can be preprogrammed into either or both controllers 20, 70. The controllers 20 and 70 may be combined into a single controller. Controllers 70 are well known in the art, and often use fiducial points to determine locations for the surgical tool to perform a desired surgical task on a designated portion of a patient.

The robotic surgical base 10 may include a surveying system, such as a LIDAR laser system, to help the robotic surgical base 10 know and understand where it is, i.e. know its location in an area or room, relative to other objects. Use of the LIDAR system helps the robotic surgical base 10 maneuver and avoid contact or collisions with objects. In addition, the surveying system could be used to allow the robotic surgical base 10 to move itself from one room to another, such as from one operating room to a second operating room, to/from a storage place, or even from one hospital to a second hospital remote from the first hospital.

What is claimed is:

1. A robotic base for a surgical robot comprising:
    a truck including a plurality of wheel assemblies rotatably mounted thereto for moving said truck on an underlying surface, said truck being adapted to have a surgical robot mounted thereon for movement therewith, at least one of the wheel assemblies including a wheel with a wheel hub and a plurality of associated rollers rotatable independently of its associated wheel hub;
    a power supply mounted to the truck;
    at least one motor carried by the truck and operably associated with a respective said wheel assembly and connected to the power supply; and
    a first electronic controller operably connected to the motor and operable to control rotation of the wheel assemblies and effect movement of the truck along a defined path.

2. The base as set forth in claim 1 wherein there are a plurality of said at least one wheel assemblies, each with a said wheel hub and said rollers, each said wheel hub and associated rollers being associated with a respective said motor.

3. The base as set forth in claim 2 wherein there being at least four said wheel assemblies, each with a said wheel hub and said rollers.

4. The base as set forth in claim 2 including a surgical robot mounted to said truck and including an electronic controller associated therewith and operable to effect operation of the surgical robot.

5. The base as set forth in claim 4 wherein the first electronic controller and the controller associated with the robot being operably connected to one another.

6. The base as set forth in claim 4 wherein the first electronic controller and the controller associated with the robot being a single controller.

7. The base as set forth in claim 4 wherein a said wheel hub and said associated rollers being independently rotatable relative to one another and selectively driven by a single associated said motor.

8. The base as set forth in claim 4 including a suspension system associate with each of said wheel assemblies, allowing components of said truck to be supported by said wheel assemblies and move independently thereof generally vertically.

9. The base as set forth in claim 8 wherein the suspension system including a plurality of fluid cylinders each associated with a respective said wheel assembly and including a pressurized fluid source operably connected to the fluid cylinders and operable to effect selective extension and retraction of the fluid cylinders.

10. The base as set forth in claim 4 wherein said motor is coupled to a respective wheel assembly with a first drive shaft and a second drive shaft with said first drive shaft being operably coupled to a respective said wheel hub and said second shaft being operably coupled to the rollers associated with said wheel hub.

11. A method of performing a surgical procedure with a robot, the method including:
    providing a truck including a plurality of wheel assemblies rotatably mounted thereto for moving said truck on an underlying surface, said truck having a surgical robot mounted thereon for movement therewith, at least one of the wheel assemblies including a wheel hub and a plurality of associated rollers rotatable independently of its associated wheel hub;
    providing a power supply mounted to the truck;
    providing at least one motor carried by the truck and operably associated with a respective said wheel assembly and connected to the power supply; and
    providing a first electronic controller operably connected to the motor and operable to control rotation of the wheel assemblies and effect movement of the truck along a defined path and effecting movement of the truck and associated robot about a surgical area with said controller.

12. The method as set forth in claim 11 wherein there are a plurality of said at least one wheel assemblies with a said wheel hub and associated said rollers, each said wheel hub and associated rollers being associated with a respective said motor and effecting operation thereof to move the truck with said controller.

13. The method as set forth in claim 12 wherein there being at least four said wheel assemblies, each with a said wheel hub and said associated rollers and controlling operation thereof with said first electronic controller.

14. The method as set forth in claim 12 including controlling operation of said surgical robot with an electronic controller.

* * * * *